(12) United States Patent
James

(10) Patent No.: US 7,037,419 B2
(45) Date of Patent: May 2, 2006

(54) CONCENTRATION OF PROTEIN AND/OR PEPTIDES SAMPLES

(76) Inventor: Peter James, Stadsbudsgatan 1 B, SE-227 36 Lund (SE)

( * ) Notice: Subject to any disclaimer, the term of this patent is extended or adjusted under 35 U.S.C. 154(b) by 32 days.

(21) Appl. No.: 10/485,718

(22) PCT Filed: Sep. 10, 2002

(86) PCT No.: PCT/EP02/10118

§ 371 (c)(1),
(2), (4) Date: Jan. 30, 2004

(87) PCT Pub. No.: WO03/025578

PCT Pub. Date: Mar. 27, 2003

(65) Prior Publication Data

US 2004/0241834 A1 Dec. 2, 2004

(30) Foreign Application Priority Data

Sep. 14, 2001 (GB) ............................... 0122200.9

(51) Int. Cl.
*G01N 27/453* (2006.01)
(52) U.S. Cl. ........................................ 204/615; 204/600
(58) Field of Classification Search ................ 204/601, 204/603, 606, 613, 615, 451, 452, 456, 461, 204/464, 465, 600
See application file for complete search history.

(56) References Cited

U.S. PATENT DOCUMENTS 5,102,518 A * 4/1992 Doering et al. ............. 204/462
5,160,626 A * 11/1992 Pemawansa et al. ........ 210/638
5,837,826 A * 11/1998 Flickinger et al. .......... 530/413
6,780,327 B1 * 8/2004 Wu et al. .................... 210/660

FOREIGN PATENT DOCUMENTS

| DE | 3913814 A1 * | 7/1990 |
| EP | 0 776 700 | 6/1997 |
| GB | 2340298 A * | 2/2000 |
| JP | 10-273498 A * | 10/1998 |
| WO | WO 94/29005 A1 * | 12/1994 |
| WO | WO 95/17955 A1 * | 1/1995 |

OTHER PUBLICATIONS

English language abstract for DE 3913814 A1.*
English language computer translation of Fukuya et al. (JP 10-273498 A).*
Clarke, N., J., et al. "One Step Microelectroelution Concentration Method for Efficient Coupling of Sodium Dodecylsulfate Gel Electrophoresis and Matrix-Assisted Laser Desorption Time-of-Flight Mass Spectrometry for Protein Anaylsis" Journal of the American Society for Mass Spectrometry, Elsevier Sceince, Inc., US vol. 9, No. 1, 1998 pp. 88-91.

* cited by examiner

Primary Examiner—Alex Noguerola
(74) Attorney, Agent, or Firm—Yonggang Ji

(57) ABSTRACT

The invention relates to a device for protein and/or peptide concentration, which device comprises electroconcentration means (23); at least two electrodes having a positive (7) and a negative charge (35), respectively; and protein and/or peptide capture means (17); wherein said electroconcentration means (23) comprises a funnel shaped cavity and at least one electrode is located on each side of the electroconcentration means. The invention also relates to a method for concentrating a protein and/or a peptide in a sample, which method can be performed in a device according to the invention.

8 Claims, 2 Drawing Sheets

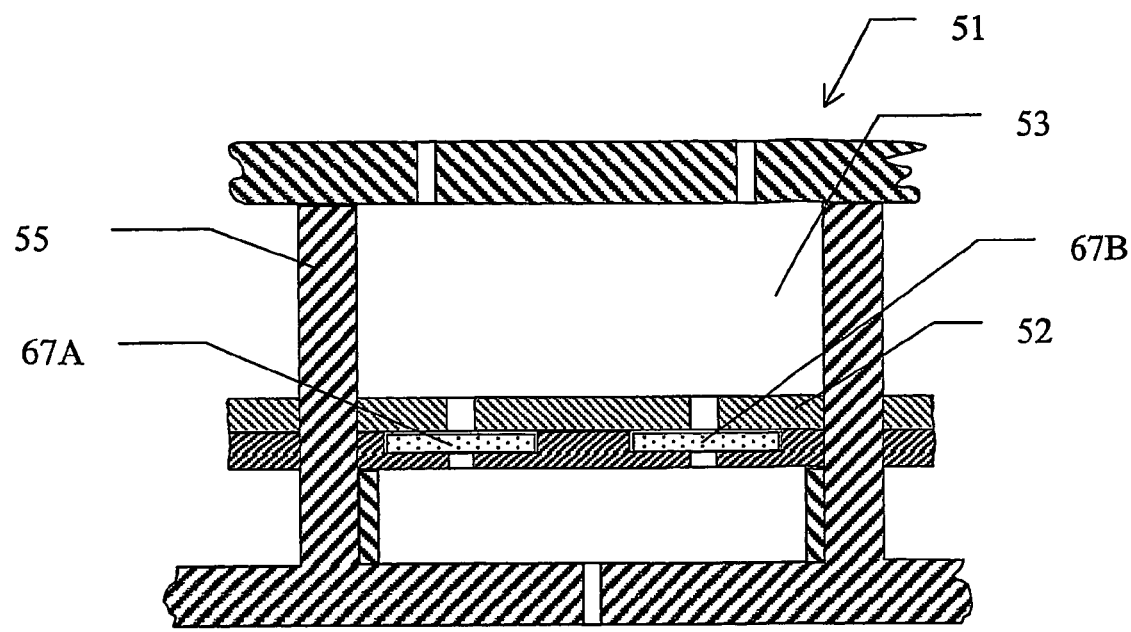
Fig. 2a)
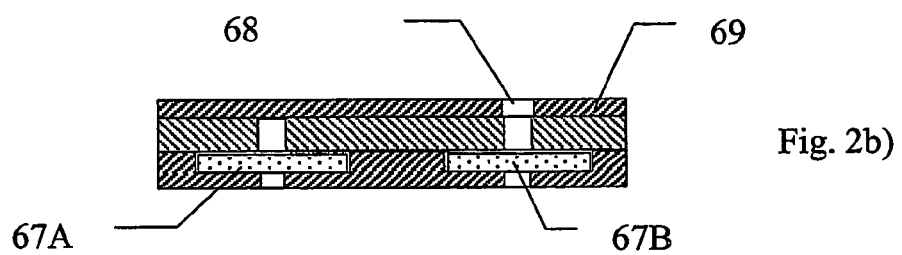
Fig. 2b)
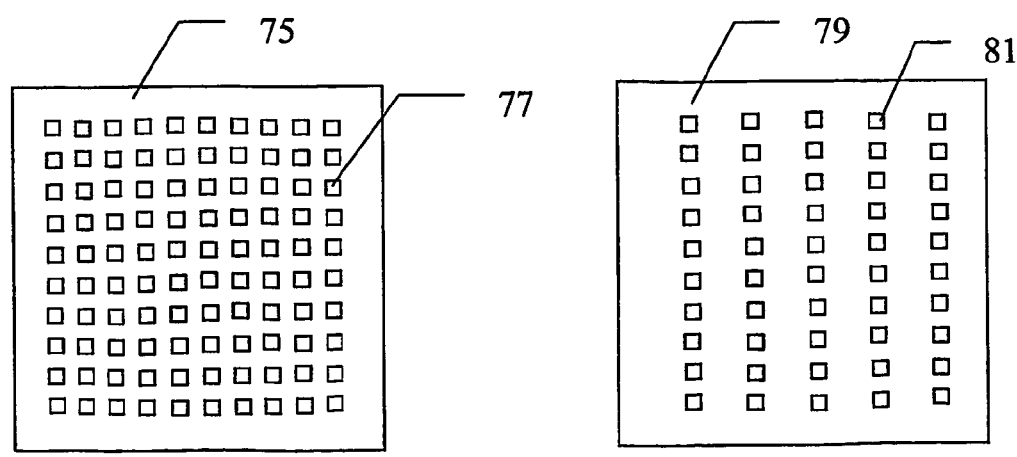
Fig 2c)                    Fig 2d)

CONCENTRATION OF PROTEIN AND/OR PEPTIDES SAMPLES

CROSS REFERENCE TO RELATED APPLICATIONS

This application is a filing under 35 U.S.C. § 371 and claims priority to international patent application number PCT/EP02/10118 filed Sep. 10, 2002, published on Mar. 27, 2003 as WO03/025578, and to foreign application number 0122200.9 filed in Great Britain on Sep. 14, 2001, the entire disclosures of which are hereby incorporated by reference.

TECHNICAL FIELD

The present invention relates to a device useful for the production, immobilisation and subsequent handling and chemical modification of small amounts of peptides prior to quantification, identification and characterisation thereof. The invention also encompasses a method for such production, immobilisation and subsequent modification.

BACKGROUND

Protein identification has been revolutionised by the introduction of methods to identify proteins in databases using mass spectral data, either based on peptide masses from protein digests or fragmentation spectra from individual peptides. Interestingly, the main problem that is encountered in high sensitivity protein/peptide analysis and identification is usually not related to the sensitivity of the analysing device (usually a mass spectrometer, which can sequence peptides at the attomole level), but the generation and handling of peptides by digestion of the protein.

In the prior art, the target protein has usually been isolated by two-dimensional gel electrophoresis (2D-PAGE) or affinity chromatography and recovered in a fairly large volume of solution, such as about 20 μl for a spot from a two-dimensional electrophoresis gel. Thus, proteins have been recovered in a very diluted state. For example, if a microgram of material is available of a 50,000 MW protein, (20 pmol) the concentration is 1 μM. This is slightly below the Km of most proteases, and even though digestion can still take place, it will be a very slow process. Further, if only a nanogram is available, i.e. 20 femtomoles which is well within the sensitivity range of modern mass spectrometers using nanospray ionisation, digestion will not occur to any significant extent since then the protein solution is too dilute.

A further drawback of the prior art devices is that the container walls, which are usually of plastics or glass, absorb peptides and proteins very easily and large losses will occur within an hour or so of the protein/peptide solution coming into contact with the container. Furthermore, subsequent handling steps such as pipetting or being loaded into a chromatography system all involve contact with large surface areas and dramatically increasing sample losses.

For a general review of the above-mentioned methods, see e.g. Staudenmann, W., Dainese Hatt, P., Hoving, S., Lehmann, A., Kertesz, M., and James, P. (1998) *Electrophoresis*, 19, 901–908. "Sample handling for proteome analysis."

SUMMARY OF THE PRESENT INVENTION

One object of the present invention is to provide a device and a method that improves handling, such as concentration, digestion and/or chemical modification, of small amounts of peptide and/or protein. Another object is to provide such a device and method wherein the peptide and/or protein immobilises directly on a surface from which a subsequent analysis can be performed by any suitable method. A further object of the present invention is to provide a device and a method for the above mentioned handling that allows it to take place with reduced losses of peptide and/or protein due to adsorption to container walls, and which thereby allows a prolonged maintenance of peptide/protein sample in the device.

The objects of the invention can be achieved by the device and method as disclosed in the appended claims.

BRIEF DESCRIPTION OF DRAWINGS

FIG. 2a) shows a schematic representation of a section through an array of flow through chemical cells for flow-through high-efficiency chemical modifications according to the present invention;

FIG. 2b) shows a partial section from the side of a target slide and mask;

FIG. 2c) shows schematically a view from above of a plate with 100 loading positions for stations of the type shown in FIG. 2a); and FIG. 2d) shows schematically a view from above of a plate with 50 loading positions.

DEFINITIONS

Figure 1A:
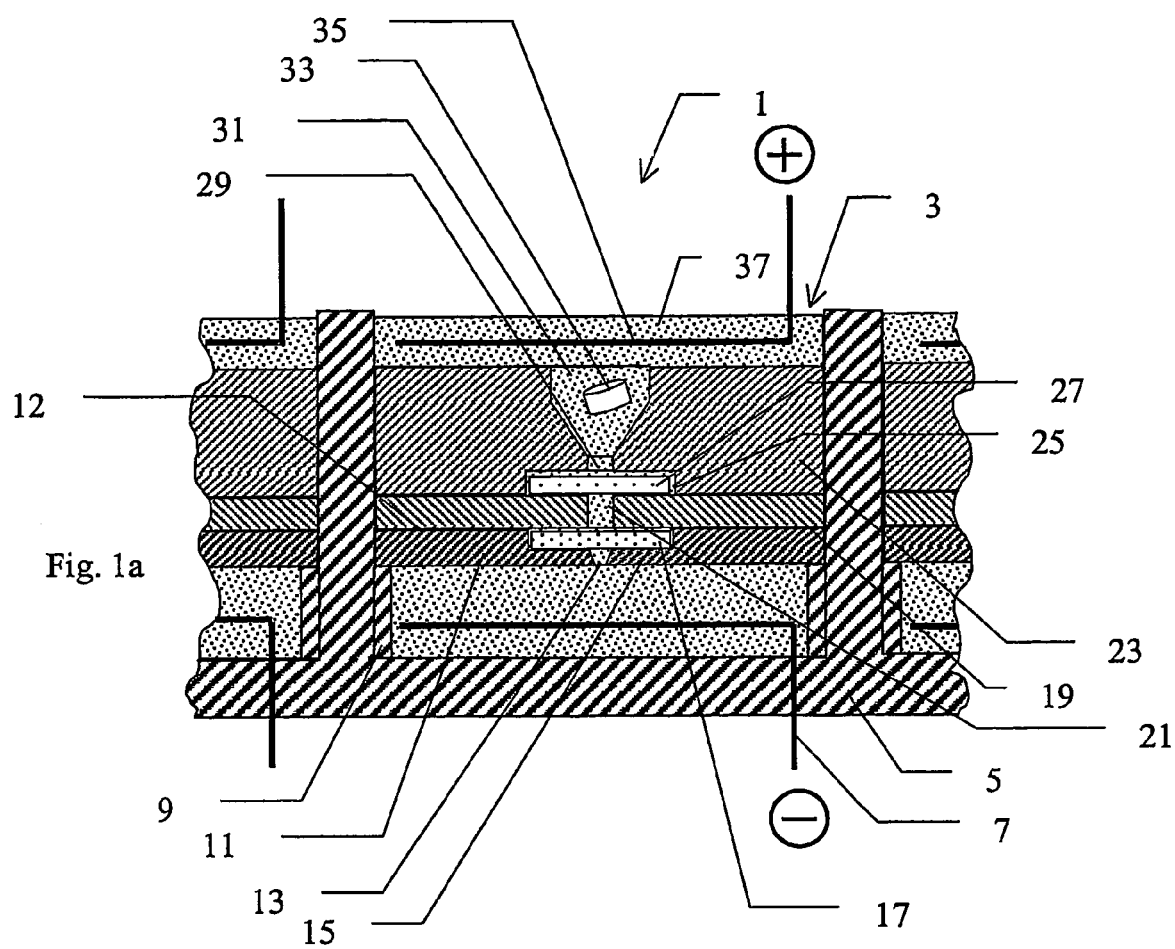
FIG. 1a) shows a schematic representation of a section though an array of devices according to the present invention for carrying out simultaneous concentration-digestion of a protein sample.

In the present specification, the term "capture" means to non-covalently bind e.g. a peptide to e.g. a support.

The term "protein and/or peptide" is understood to include any chain of amino acids or modified forms thereof.

DETAILED DESCRIPTION OF THE INVENTION

A first aspect of the present invention is a device for protein and/or peptide concentration in a sample, which device comprises:

electroconcentration means comprising a funnel shaped cavity with a wide end and a narrow end; at least two electrodes, one electrode being positioned near to said wide end and one electrode being positioned nearer to said narrow end; and one or more protein and/or peptide capture means; wherein said capture means is located between said narrow end and said one electrode positioned near said narrow end.

In the preferred embodiment, the present device is presented as an assembly held together by a seal. During use, the whole device is preferably held within a pressurised container at around 2–3 bar to prevent the formation of bubbles which otherwise might form during electrophoresis from blocking the passages and stopping the current flow.

The sample can be presented to the device in an electroelution chamber which chamber is present in an electroelution bath. The electroelution chamber can be fixed, e.g. by clamps, to an analysis target, such as a MALDI target, for subsequent analysis.

The types of material used to make device may vary according to the mode of analysis. Thus, the electroelution bath can be made from any material that shows a sufficiently low protein absorbance and which is also preferably easy to machine, such as Plexiglas. The same criteria for material properties can also be applied to the electroconcentration means. Electrodes, clamps, and analysis target can be made from a chemically inert metal such as stainless steel or a metal coated with a noble metal such as gold. The seal can be any flexible material such as silicone rubber tubing. The capture means includes a trapping material such as C18 silica embedded in Teflon discs, since these are mechanically stable and very chemical resistant. This allows one to carry out chemical reactions such as chemical digestions in the gas phase with reagents such as cyanogen bromide, pentafluoropropionic acid and S-ethyltrifluoroacetate. However, other trapping materials can be used and are easily selected by the person skilled in this field according to the method of analysis to be used subsequently. In a specific embodiment, the analysis target, which is constituted of pieces of metal, is made of chemically resistant metal when the sample is going to be analysed by MALDI-TOF mass spectrometry, since one has to fix the membrane at a defined potential in the instrument. Otherwise other materials may be used depending on the analysis method to be used. In one embodiment, the analysis target contains a heating element so the digest temperature can be maintained at about 37° C. In an alternative embodiment, the temperature is controlled with an external heating source. An advantageous feature of the invention is that there may be 'teeth', or a raised edge, around each hole holding the capture means, providing a minimal or even no cross flow of reagents or samples. Other elution formats can be used, e.g. a dual elution chamber.

In one embodiment of carrying out the present invention, the protein(s) and/or peptides are equilibrated with a detergent or solubilising agent such as sodium dodecyl sulphate or urea, until they are fully in solution. However, the protein(s) and/or peptides can alternatively be present either in a gel slice, such as a 2D gel spot, or attached non-covalently to any other carrier. The protein-containing sample is then placed in the funnel of the electroconcentration funnel block.

The volume of the funnel shaped cavity can be designed to accommodate any volume but a volume of between about 0.5–10 ml, which corresponds to the range of commonly used sample volumes, is preferably used. The funnel inlet size is not critical, however the size of the narrow, outlet end of the funnel is important for two reasons. Firstly, it is the volume of the outlet end part of the funnel shaped cavity that defines the final concentration of the material undergoing digestion. Since the Km of most proteolytic enzymes is in the range 5–50 µM, digestion of proteins will only be effective in the pmol/µl range. For example, the narrow end of the funnel shaped cavity should have a volume of less than about 100 nl if protein amounts are in the hundreds of femtomoles region As the person skilled in this field realises, it should be proportionately smaller if the amount to be digested is less. Secondly, the diameter of the outlet hole defines the area of peptide/protein capture, which is the area that will be subsequently used for analysis. The smaller the area, the higher the concentration of digested or concentrated material, and hence the higher the sensitivity in applications such as matrix-assisted laser desorption and ionisation (MALDI) mass spectrometry (MS), fluorimetry (for fluorine labelled material) or various antibody based detection methods. The minimum size is defined by detection method, for example with MALDI-MS, the size of the laser spot. Practical experience defines the minimum useful size i.e. the narrowest point of the funnel next to the MS cut-off membrane, in this configuration to be around 30 µm.

Thus, in one embodiment described below, the dimension of the outlet of the narrow end of the funnel shaped cavity of the device has been adapted to the envisaged method of analysis.

Thus, the present invention discloses a device that allows the concentration, digestion and/or chemical modification of very small amounts of protein and/or peptide and immobilises them directly on a surface from which they can be subsequently analysed by the method of choice.

In accordance with the present invention, concentration of an isolated protein or proteins can be obtained down to a final volume of around 20–100 nl or lower, as compared to the prior art, where digestion has usually been performed in the gel spot which is around 20 µl or on a electroblotting support which requires around 5 µl.

In one embodiment of the present device, the capture means is in the form of an immobilisation support capable of capturing positively and/or negatively charged peptides. In other embodiments, specific immobilisation supports can be created by using antibodies, affibodies etc. Alternatively, specific binding properties of proteins can be used and ion exchange or specific immobilised metal ion chromatography (IMAC) supports can be used to capture acidic, basic or phosphopeptides.

In one advantageous embodiment of the present device, the funnel shaped cavity of the electroconcentration means is in a position wherein said cavity has its longitudinal axis in an essentially vertical position, with the wide end above the narrow end.

The present device can be operated in two different modes. The first of these embodiments is advantageously used when proteolysis is carried out using an enzyme or when peptides are to be extracted from a mixture comprising higher molecular weight molecules. The device according to the invention then further comprises a semi-permeable restriction membrane or a size cut-off membrane positioned in the peptide's path such that peptides must pass through the membrane before they can reach the capture means. The membrane can be made of cellulose acetate and to make the pores smaller and stabilise the structure both mechanically and chemically, it can be treated e.g. with acetic anhydride. Alternatives include any materials that can be made with a defined pore size range such as silica glass or a polymer such as acrylamide and these can be made as an integral part of the device rather than just as a membrane. When using this embodiment, a sample is placed in the device, an enzyme, such as a protease, is added and the sample is co-concentrated. The proteins remain in solution and can now be efficiently digested by the enzyme since they are now very much more concentrated. A membrane (available from a number of commercial sources, such as Spectrapore inc.) with a molecular cut-off weight e.g. of around 3000 Dalton will then be placed between the protein solution and the capture means. Thus, only smaller peptides which are amenable to MS/MS analysis are trapped in the capture means and any large molecules such as polymers like PEG or big proteins which interfere with the MS analysis will be removed by the cut-off membrane. The proteins concentrate above the cut-off membrane but cannot pass through it, however the peptides being released during digestion can pass through it and are subsequently immobilised on a capture membrane prior to subsequent handling.

In the second embodiment, the present device can be operated without a membrane. This is especially advantageous when the captured protein or peptide is to be digested with a chemical and the concentration factor is determined by the diameter of the end of the concentration funnel.

Suitable chemicals for this purpose are e.g. cyanogen bromide, pentafluoropropionic acid or S-ethyltrifluoroacetate. For example, in order to digest femtomole amounts of material the protein must be concentrated from the usual 1 fmol/µl range up to the pmol/µl range.

Thus, in one embodiment, the present device is especially adapted for tagged proteins. In this embodiment, the present device comprises two capture means separated from each other, one of which is preceded by a mask allowing unmodified peptides to pass through and the other one of which is preceded by a mask allowing modified peptides to pass through and adapted to generate a peptide fingerprint by ladder chemistry. In this embodiment, the tag is the sequence generated by ladder chemistry, which is a well known concept to those skilled in this field. The chemistry preferably used herein is thioacetylthioester degradation similar to the well known Edman degradation. More detailed, it is setup to be inefficient so 20% or so of the N-terminal amino acid of a peptide is removed. This is repeated ×3 to give some 40% intact peptide 1, 30% peptide 1—1 amino acid, 20% with two amino acids removed and 10% with one amino acid removed. By the mass differences between the peaks in the MS one can read a sequence. For example, if the parent peptide mass 1000, −1aa mass 943, −2aa 830, −3aa 701, then the sequence tag is 1000, glycine, leucine, glutamic acid.

In an advantageous embodiment, the capture means, e.g. the membrane support, can subsequently be used as a flow-through reactor to allow high efficiency chemical modifications of very small amounts of material and/or can be used directly for analysis by mass spectrometry, functional activity assays or fluorescence detection for example. The device can be operated in parallel allowing large numbers of proteins to be concentrated, digested and immobilised on a membrane for subsequent modification and/or analysis. Accordingly, the device according to the present invention is especially suitable for automated procedures, where it will enable substantial savings in process time and costs, as compared to the prior art methods. Thus, in one embodiment of the present device, the capture means are adapted for use in MALDI-MS.

In the experimental part below, one illustrative embodiment of a device according to the present invention will be described in more detail with reference to the drawings. As the person skilled in this field will realise, the present device can however be constructed in alternative fashions for example, as a silicon chip, as arrays, as single units, as disposable units, as reusable units, etc. In all cases, the principle remains the same, namely, the concentration of the protein in the liquid phase to allow digestion or capture on an immobilising surface for subsequent analysis.

A second aspect of the present invention is a method for concentrating a protein and/or a peptide in a sample, comprising the steps of (a) Providing a sample which comprises proteins and/or peptides and a digestive agent in an electrophoresis device, wherein the electroelution bath is present in an essentially funnel shaped cavity;

(b) Applying a voltage between at least two electrodes located on each side of said electroelution bath to pass peptides towards a capture means located between the narrow end of said funnel shaped cavity and the electrode positioned nearer said narrow end;

(c) Changing the direction of the voltage at least once to provide oscillations enabling both positively charged and negatively charged peptides to contact the capture means; and, (d) Collecting concentrated peptides from the capture means.

The voltage causes the proteins and peptides to move in a certain direction and the speed of movement is inversely proportional to the size so proteins remain essentially where they are since they are negatively charged due to detergent such as SDS present in the sample. Once digested, the resulting peptides can be positively or negatively charged. Hence, without reversal of the voltage occasionally, one set will be lost, since then they move away from the capture membrane. Usually, the actual digestion during the first voltage will last for a longer time, such as a couple of hours, as compared to the subsequent changes of the voltage direction, which changes can be made more often, e.g. every 10 minutes. However, the exact intervals and reaction times are easily determined by the skilled in this field for each desired concentration procedure.

In one embodiment of the present method, the digestive agent is an enzyme, preferably a protease (such as trypsin, V8 protease, LysC, AspN etc) or a glycosidase to release O- and N-linked saccharides for capture on a hydrophilic support prior to subsequent analysis of the glyco-portion.

In another embodiment of the present invention, the method above is adapted to comprise the further step of separating larger size molecules, such as proteins, from smaller size molecules, such as peptides, by introducing a size cut-off membrane between the narrow end of the funnel shaped cavity and the capture means. The membrane is there to prevent proteins from reaching the capture means during the digestion and also at the end of the digestion, when the sample is conveniently allowed to flow downwards through the device. Thus, it prevents any large fragments from coming onto the membrane. In this context it is understood that the term "large" refers to fragments of an undesired size, and that the cut-off value of the membrane is selected depending on the desired size of peptides.

In one embodiment of the present method, in step (b), the sample is divided after the funnel shaped cavity into two or more parts and each part is passed towards a separate capture means, one capture means being preceded by a mask allowing unmodified peptides to pass through and the other one being preceded by a different mask allowing modified peptides to pass through, and in step (d), unmodified peptides are collected from one capture means and tagged peptides providing a peptide fingerprint are collected from another capture means. Thus, tagging is allowed, as discussed above in relation to the device. Since each digest generates a set of peptide masses, known as the peptide fingerprint, one can use this to identify a protein in a database that generates a similar theoretical set of peptides when digested by the same enzyme. This is known as 'peptide mass fingerprinting'. However, in the prior art, this has often shown to be not enough for a reliable identification. Thus, the present invention now allows one to generate a peptide fingerprint as well as a small sequence of three amino acids per peptide. This allows proteins to be identified at a much greater confidence level and far more efficiently than previously. For details to this end, the tagging technology has been described: for an algorithm for identification using sequence tags and the method to generate them using exopeptidases, see Korostensky, C., Staudenmann, W., Dainese, P., Hoving, S., Gonnet, G., and James, P. (1998) Electrophoresis, 19, 1933–1940. "An algorithm for the identification of proteins in sequence databases using peptides with ragged N- or C-termini generated by sequential endo- and exopeptidase digestions", and for a description of the method of generating the tags chemically, see Hoving, S., Münchbach, M., Quadroni, M., Staudenmann, W., and James, P. (2000) Anal. Chem. 72, 1006–1014. "Multiple N-terminal tag generation from unseparated protein digests using a novel thioester based degradation reaction".

In a specific embodiment, the peptide fingerprint is generated by thioacetylthioester degradation. This can also be carried out by Edman degradation using phenylisothiocyanate or any other suitable reagent with an isothiocyanate moiety.

In an additional embodiment of the method, the proteins and/or peptides to be concentrated are present in a gel or in a solution. Alternatively, they can be non-covalently bonded to a support. The enzyme can e.g. be added to the sample in the electroelution bath before applying the voltage to digest proteins into peptides or can be rehydrated to the gel piece.

One specific embodiment of the present method is a method according to the invention which is suitable for analysis of a protein and/or peptide sample and which comprises the further step of inserting the capture means obtained in step (d) into a detection apparatus, such as a MALDI-MS. In this context, phosphorylation and glycopeptide elimination analysis can advantageously be used. For more details to this end, a method for phosphorylation analysis that is done in a test tube has been described, see Quadroni, Q. (2000) Principles and Practice. *Proteome Research: Mass spectrometry*. Specific detection of analysis of phosphorylated peptides by mass spectrometry, pp 187–206. Wiley-Springer Verlag. Ed. James, P.

An advantageous embodiment of the present method uses a device according to the invention as described above.

Thus, in summary, in one illustrative embodiment of the present method, a sample comprising proteins is first equilibrated as described above and enzyme, such as protease or a digestive chemical is added. The electrophoresis is started after said addition. The sample is focused onto a low molecular weight cut-off membrane as discussed above and then the polarity of the voltage is reversed once or several times, e.g. every five or ten minutes for one hour. The fragments which are small enough to pass the first membrane migrate very quickly (since they are small) onto the C18 membrane where they are immobilised. The buffers are preferably removed from the bath and then water is passed through from top to bottom through the immobilising support to remove undesired salts. In one embodiment the present method also comprises a step of analysis, wherein the device is then disassembled and inserted into the measuring device of choice. For example, if the sample is to be measured by MALDI, the support is inverted and about 1–2 μl of MALDI matrix such as α-cyano-4-hydroxy-cinnamic acid, 10 mg/ml in 80% acetonitrile, 1.25% TFA in water is added and allowed to flow into the membrane. The support is then suitable for being placed into the MALDI-MS. In an alternative embodiment, the support can be used as a nano-electrospray tip. The bottom end of each channel leading out of the MALDI target can be made in a sharp conical form with about 10 μm diameter outlet. In this context, it is understood that the term "sharp conical form" means a conical shape with a hole in the centre, wherein the walls of the exit point around the hole are very narrow/sharp i.e the internal angle of the cone is preferably less than, 45° and most preferably 30° or less. A high-pressure liquid chromatography line can be clamped across the target and a gradient ran out to allow HPLC-MS measurements. Another embodiment utilises a double trapping layer with C18 particles first and then a strong cation exchanger. The sample can be measured using MALDI first and then the matrix washed away by any suitable solution leaving the peptides bound to the strong cation exchanger and eluting the peptides with a suitable gradient of e.g. acetonitrile in water with TFA or formic acid.

In summary, the present invention describes a novel device and method, which compared to the prior art gel-based concentration system for the concentration of proteins from 2D gels includes the following advantages:

According to the present invention, there is no need to stain the sample. In the prior art, the protein must be stained to be visualised and this causes losses during fixing, as well as time consuming staining and destaining steps, especially with small proteins. Even though protein could be collected without staining by reference to its position relative to a dye front, this is unreliable and leads to larger volumes of gel being cut out in order to ensure complete recovery of the proteins.

Further, according to the present invention, proteins are easily accessible to proteases and digestive chemicals, as compared to the prior art methods, where protein trapped in the polymer matrix can remain inaccessible to proteases.

In the prior art methods, the buffers and detergents present disturb HPLC and MS analysis and must be removed to allow high sensitivity analysis causing further losses. There is no such need according to the present invention.

Finally, subsequent pipetting and transfer steps as well concentration by lyophilisation required in the prior art cause further sample losses. Another sample loss is especially critical, namely the loss of phosphopeptides onto metal surfaces, such as inside of metal HPLC columns, frits at the beginning and end of columns, injection valves etc. Such losses are also avoided according to the present invention.

The present invention will now be described by way of examples, which are provided for illustrative purposes only and which should not be construed as limiting the invention as defined by the appended claims. All references given below and elsewhere in the present application are hereby included herein by reference.

EXPERIMENTAL PART

Example 1

Device for Digestion

Figure 1B:
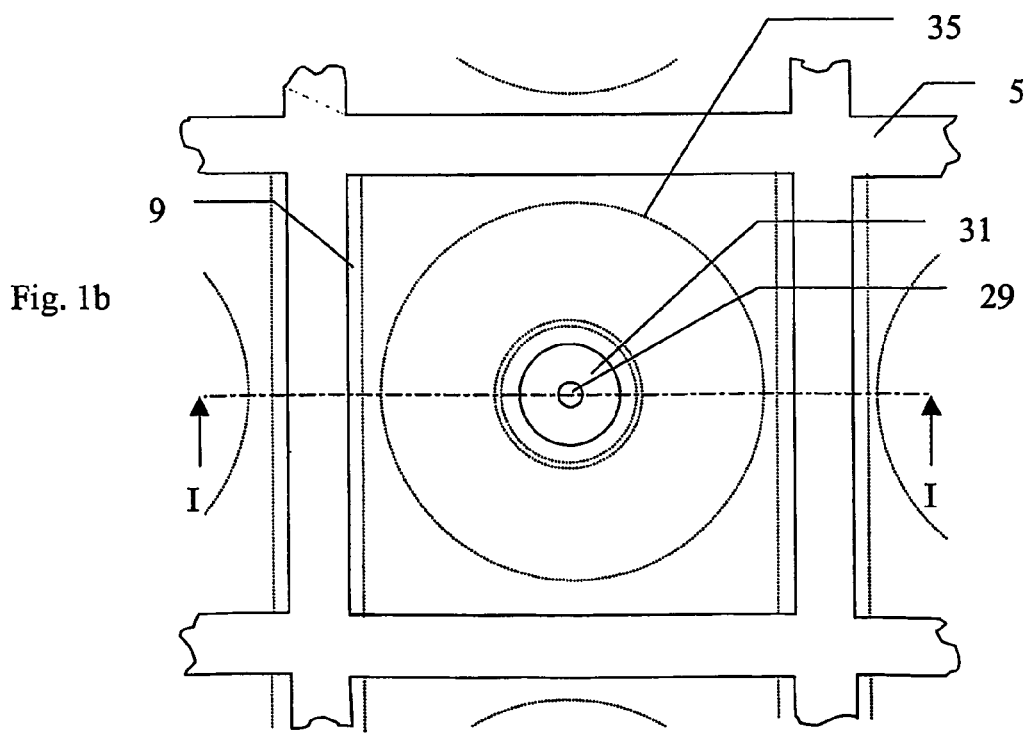
FIG. 1b) shows a view from above of the array of FIG. 1a)

A device according to the invention, which is especially adapted for use with MALDI, is described below with reference to FIGS. 1a) and 1b). FIG. 1a) shows schematically a section through part of an array 1 of substantially identical electroconcentration cells 3 formed in a substrate 5 and FIG. 1b) shows a view from above of the section of FIG. 1a). The array may comprise any suitable number of cells, preferably arranged in a grid pattern comprising a number of rows and columns, for example 8 rows and 12 columns or 10 rows and 10 columns, etc. The construction of one such cell shown in FIG. 1a) and FIG. 1b) will now be described. Cell 3 is preferably formed as a regularly shaped cavity 3, in this example a cube, formed in said substrate 5. A first electroconcentration electrode 7, connected to a power supply (not shown) is provided at the lower part of cavity 3. A spacer means in the form of a wall 9 or the like, projecting a small distance towards the centre of cavity 3 and extending a distance from the base of the cavity 3 that is sufficient to contain first electrode 7, supports a MALDI target slide 12. MALDI target slide 12 comprises first and second thin square sheets 11,19 of conducting material such as stainless steel, aluminium or the like, which are placed with second upper sheet 19 on top of, and in contact with first, lower sheet 11. Sheets 11, 19 are joined together by any suitable means such as gluing, welding, brazing, crimping, folding, riveting, being bolted together, etc. Sheets 11, 19 have sides which are as long as or slightly smaller than the lengths of the inner walls of cavity 3 such that MALDI target slide 12 can fit inside cavity 3. Preferably the dimensions of MALDI target sheets 11, 19, wall 9 and cavity 3 are adapted so that when MALDI target slide 12 is positioned on wall 9 no fluid can flow past the outer edges of the MALDI target slide 12. Seals, not shown, may also be provided as necessary to accomplish this. MALDI target lower sheet 11 has a central though hole 13 which opens into a cylindrical cut-out 15 on the upper surface of lower sheet 11. A capture means 17 in the shape of a disc having a diameter less than the diameter of cut-out 15 and a height less than or equal to the height of cut-out 15 is positioned in cut-out 15. Capture means can be in the form of a semi-permeable membrane, e.g. comprising C-18 silica particles in a Teflon™ membrane, which can capture molecules of interest. Second, upper sheet 19 has a central through hole 21 that is arranged to be substantially concentric with the through hole 13 of first sheet 11. An electroconcentration block 23 made of a chemically inert, insulating material such as Plexiglas™ is positioned on top of, and in sealing contact with second, upper sheet 19. Block 23 has sides, which are as long as or slightly smaller than the lengths of the inner walls of cavity 3 such that block 23 can fit inside cavity 3. The height of block 23 is sufficient to contain a digestion funnel and membrane as described below. The bottom surface of block 23 which is in contact with the upper surface of upper sheet 19 of the MALDI target slide 12, has a cylindrical central cut-out 25 that is substantially concentric with the cut-out 15 of lower sheet 11. Cut-out 25 contains a weight cut-off membrane, e.g. a 3000 Da molecular weight cut-off membrane 27. Block 23 further comprises a channel 29, substantially concentric with though holes 13, 21. Channel 29 extends from cut-out 25 and forms the narrow spout of an inverted-cone-shaped electroconcentration funnel 31 formed in block 23. The upper, wider end of funnel 31 is sufficiently wide enough to receive a gel sample 33, and will in general be of a size of about 1–10 mm in diameter, and funnel 31 tapers down to the diameter of channel 29. A second electrode 35 is positioned above block 23 and is immersed in bath fluid 37. Bath fluid fills the cell 3 so that first electrode 7 is in electrical contact with second electrode 35.

The whole device is held within a pressurised container at around 2–3 bar to prevent bubble formation during electrophoresis from blocking the passages and stopping the current flow.

The weight cut-off membrane 27 is preferably made of cellulose acetate, which has been acetic anhydride treated. The trapping material for the capture means 17 is C18 silica embedded in Teflon discs (known as "Empore™"), which allows one to carry out chemical reactions such as chemical digestions in the gas phase with reagents such as cyanogen bromide, pentafluoropropionic acid and S-ethyltrifluoroacetate. The MALDI target (i.e. the sheets 11, 19 between which the Empore membrane is clamped) is made of chemically resistant metal since in MALDI-TOF mass spectrometry one has to fix the membrane at a defined potential in the instrument. The MALDI target can contain a heating element (not shown) so the digest temperature can be maintained at a desired temperature, e.g. 37° C. The molecular weight cut-off membrane 27 and the C18-Teflon material are each one membrane, which covers the entirety of the target. There is no cross flow of reagents or samples since 'teeth' or a raised edge around each hole holds the membranes.

The electrophoresis is started after the addition of proteolytic enzyme. The protein and enzyme are focused onto the low molecular weight cut-off membrane by using a potential difference between the electrodes of 300V for 2 hours, and then the polarity of the voltage is reversed every five minutes for one hour. The fragments which are small enough to pass the first membrane 27 migrate very quickly (since they are small) onto the C18 membrane 17 where they are immobilised. The buffers are removed from the bath and then water is passed through from top to bottom through the immobilising support to remove salts. The device is then disassembled, the MALDI target is inverted and 1–2 µl of MALDI matrix in the form of α-cyano-4-hydroxy-cinnamic acid, 10 mg/ml in 80% acetonitrile, 1.25% TFA in water is added and allowed to flow into the membrane 17. The target is then placed into a MALDI-MS. In this embodiment, preferably the bottom end of each though hole leading out of the MALDI target is made with a sharp conical form with a 10 µm diameter exit (for reasons of clarity of illustration, these holes are not drawn to scale in the figures). A high-pressure liquid chromatography line is clamped across the target and a gradient ran out to allow HPLC-MS measurements.

Example 2

Concentration of Peptides

Conditions for sample solubilisation from gels: The protein cut from the gel contains 0.1% SDS if cut from a non-fixed gel (covalent fluorescent staining or reversed staining) or 0% SDS if fixed and washed (silver, Coomassie etc stains). Stained proteins are solubilised by leaving the gel overnight in 3% SDS. The final concentration in the gel for both sample types is between 0.001–0.03%. This helps saturate the surfaces of the device lowering absorption and increases the mobility of the protein.

Experimental description: Ten proteins (horse heart cytochrome c, recombinant whale myoglobin, calmodulin, bovine serum albumin, and six subunits (30S subunits S1, S2, S4, S8, S11, and S16) of the small 30S ribosome from *Escherichia coli*) were digested at varying concentrations either in solution in an Eppendorff tube or in the device. The digestions were carried out in all cases with 0.1 µg of trypsin in 100 mM ammonium bicarbonate and 0.001% SDS at 37° C. in a volume of 10 µl in the Eppendorff or added to the device. A voltage of 300V was applied for 2 hours after loading and the device was maintained at 37° C. After two hours the polarity of the voltage was reversed every 10 minutes for the next four hours. The solution digestion was stopped after six hours by passing the solution through an Empore C18 membrane. The peptides were eluted using 5 µl of 60% acetonitrile, 0.1% trifluoroacetic acid in water and the entire 5 µl was loaded onto the MALDI target by multiple spotting and drying onto a surface precoated with matrix and the mass spectrum was measured. The digestion in the device was stopped by removing the voltage and bringing the solution to flow through the immobilising support in the device. The device was disassembled and matrix in 80% acetonitrile was spotted onto the immobilising support on the side that was not in contact with the protein solution.

Summary of results averaged obtained from the ten proteins:

| Protein concentration (pmol/µl) | Average number of peptides in spectra (from 800–3000 m/z) (excluding tryptic autoproteolytic fragments) obtained from the ten proteins | |
| --- | --- | --- |
| | In solution | In device |
| 100 | 24 | 23 |
| 10 | 24 | 24 |
| 1 | 20 | 22 |
| 0.1 | 10 | 22 |
| 0.01 | 3 | 23 |
| 0.001 | 0 | 17 |

Example 3

Ribosomal Protein Isolation

*Escherichia coli* MC4100 (F-araD139 D(argF-lac) U169 rpsL150 relA1 deoC1 ptsF25 rpsR flbB5301) was obtained from the laboratory collection. Bacteria were cultivated in a sulphur-free, synthetic glucose-salts medium as previously described, with the addition of 500 µM inorganic sulphate. The cultures were grown aerobically on a rotary shaker (180 rpm) at 37° C., and growth was monitored spectrophotometrically at 650 nm. Cells were harvested in the mid-exponential phase ($A_{650}$=0.5) by centrifugation (7,000×g, 10 min, 4° C.) and washed with 50 mM Tris/HCl, pH 7.0. They were then resuspended in the same buffer (0.8 g wet mass per ml) and ruptured by three passages through a chilled French pressure cell at 135 MPa. 10 µl of 10 mM Tris/HCl, pH 7.5 was added per 200 µl of pellet, followed by 20 µl of 150 mM DTT. DNase I (50 µg/ml) and RNase A (10 µg/ml) were added and incubated for 30 min at 37° C. Cell debris was removed by centrifugation (12000×g, 30 min, 4° C.). The supernatant was centrifuged for 2 hours at 45,000 rpm at 4° C. The pellet was resuspended in 5 ml high salt buffer (20 mM Tris-HCl, pH 7.0, 400 mM NH$_4$Cl, 10 mM MgAc$_2$, 6 mM β-mercaptoethanol) and layered onto a 7 ml 17.5% sucrose cushion and centrifuged for 3 hours at 45,000 rpm at 4° C. The pellet was resuspended in a low Mg$^{2+}$-buffer (10 mM Tris-HCl, pH 7.5, 30 mM NH$_4$Cl, 0.3 mM MgCl$_2$, 6 mM beta-mercaptoethanol) and contained mostly intact ribosomes. MgCl$_2$ and acetic acid were added to final concentrations of 66 mM and 67% (v/v) respectively and the solution was incubated on ice for 1 hour followed by centrifugation for 10 min. at 10,000 rpm. The pellet was redissolved in the same solution and the extraction procedure was repeated once. The supernatants were combined and dried in the speed-vac.

Before separating the ribosomal proteins by reversed-phase HPLC, the rRNA was extracted. MgCl$_2$ and acetic acid were added to the ribosomes to a final concentration of 67 mM and 67% respectively and then incubated on ice for 1 hour. The mixture was centrifuged at 10,000 rpm for 10 min. at 4° C. in a Sorvall SS-34 rotor. The procedure was repeated once more with the pellet. The supernatants were combined and concentrated in the speed-vac. The proteins were redissolved in 3% acetic acid, centrifuged at 10,000 rpm for 20 minutes at room temperature in an Eppendorff centrifuge to remove any undissolved particles and injected onto a preparative reversed-phase HPLC system (L-6220 Intelligent Pump, L-4250 UV-VIS Detector, Merck-Hitachi AG, Darmstadt, Germany). A gradient of 10–25% B in 30 min., 25–35% B in 40 min., 35–36% B in 30 min., 36–40% B in 40 min., 40–55% B in 60 min. and 55–90% B in 40 min. was run at 2 mL/min. (A=0.1% TFA, B=80% acetonitrile/ 0.08% TFA), using a $C_{18}$ preparative column (250×21 mm, Nucleosil 100—12 µm, Macherey-Nagel AG, Oensingen, Switzerland). The absorbance was measured at 220 nm. Fractions of 2 mL were collected and the amount of protein determined by the method of Lowry and the proteins were identified by HPLC-MS/MS analysis of tryptic digestions of the fractions.

Example 4

The Immobilised Membrane as a Flow-Through Chemical Reactor

Sequence Tagging: The chemistry of the method for sequence tagging was as disclosed in Hoving, S., Münchbach, M., Quadroni, M., Staudenmann, W., and James, P. (2000) *Anal. Chem.* 72, 1006–1014. Multiple N-terminal tag generation from unseparated protein digests using a novel thioester based degradation reaction.

FIG. 2a) shows schematically a section through part of an array 51 of substantially identical flow-through chemical reactor cells 53 formed in a substrate 55, ands FIG. 2b) shows a MALDI target slide and masking plate as described below. The array 51 may comprise any suitable number of cells, preferably arranged in a grid pattern comprising a number of rows and columns, for example 5 rows and 10 columns, 8 rows and 12 columns or 10 rows and 10 columns, etc. The construction of one such cell 53 shown in FIG. 2a) will now be described. Cell 53 is preferably formed as a regularly shaped cavity 53, in this example a cube, formed in said substrate 55. The dimensions of the cavity are adapted to the dimensions of a capture means support e.g. a MALDI target slide 52 similar to the MALDI target slide 12 described above but in this instance supporting a plurality, e.g. two, of capture means 67A and 67B. Capture means 67A and 67B are spatially separated and provided with sealing means (not shown) in order to prevent transferring of substances from one capture target to the other. For the Tagging method it is envisaged that two passageways exit from a gel-loading funnel similar to that described in connection with FIG. 1 described above, one passageway leading to capture means 67A and the other passage way leading to capture means 67B. The protein is more or less equally divided between the two capture means 67A and 67B. In the subsequent chemical tagging experiment in the cell 53 a masking means such as an inert Teflon masking plate 69, as shown in FIG. 2b), provided with a though hole 68 is positioned over the slide 52 such that one of each pair of capture means, e.g. capture means 67A is masked by the portion of a masking means 69 which does not have a through hole, and does not undergo degradation whilst the other capture means 67B has the through hole 68 positioned above it and therefore is able to be degraded. Thus an intact digest is present which defines the parent peptides in the tagged position allowing easier data extraction. FIG. 2c) shows schematically a view (not to scale) from above of a plate 75 with 100 loading positions 77 for stations of the type shown in FIG. 2a); and;

FIG. 2d) shows schematically a view (not to scale) from above of a plate 79 with 50 loading positions 81. The above mentioned embodiments are intended to illustrate the present invention and are not intended to limit the scope of protection claimed by the following claims.

What is claimed is:

1. A device for protein and/or peptide concentration in a sample, which device comprises
   means for electroconcentrating (23) including a funnel shaped cavity (33) with a wide end and a narrow end;
   at least two electrodes (7, 35), one electrode (35) being positioned near to said wide end and one electrode (7) being positioned nearer to said narrow end;
   one or more means for capturing proteins and/or peptides (17) located between said narrow end and said one electrode positioned near said narrow end; and
   a size cut-off membrane (27) positioned above the capture means (17) capable of separating non-digested proteins from peptides, or larger size peptides from smaller size peptides.

2. The device of claim 1, wherein the capture means are adapted for use in MALDI-MS or MALDI-TOF.

3. The device of claim 1, wherein the capture means (17) is an immobilization support capable of capturing positively and/or negatively charged peptides.

4. The device of claim 1, wherein the funnel shaped cavity (33) of the electroconcentration means (23) is in a position wherein said cavity is located in an essentially vertical position, the wide end being in a higher position than the narrow end.

5. A device for protein and/or peptide concentration in a sample, which device comprises
   means for electroconcentrating (23) including a funnel shaped cavity (33) with a wide end and a narrow end;
   at least two electrodes (7, 35), one electrode (35) being positioned near to said wide end and one electrode (7) being positioned nearer to said narrow end;
   two means for capturing proteins and/or peptides (17) located between said narrow end and said one electrode positioned near said narrow end: and said two capture means (67A, 67B) separated from each other, one of which is preceded by a mask allowing unmodified peptides to pass through and the other one of which allowing modified peptides to pass through.

6. The device of claim 5, wherein the two capture means (17) are immobilization support capable of capturing positively and/or negatively charged peptides.

7. The device of claim 5, wherein the funnel shaped cavity (33) of the electroconcentration means (23) is in a position wherein said cavity is located in an essentially vertical position, the wide end being in a higher position than the narrow end.

8. The device of claim 5, wherein the capture means are adapted for use in MALDI-MS or MALDI-TOF.

* * * * *